(12) United States Patent
Orloff et al.

(10) Patent No.: US 6,783,502 B2
(45) Date of Patent: Aug. 31, 2004

(54) INTEGRATED LANCING AND ANALYTIC DEVICE

(75) Inventors: Eugene L. Y. Orloff, Berkeley, CA (US); Kumar Subramanian, Pleasanton, CA (US)

(73) Assignee: Phoenix Bioscience, Pleasanton, CA (US)

( * ) Notice: Subject to any disclaimer, the term of this patent is extended or adjusted under 35 U.S.C. 154(b) by 230 days.

(21) Appl. No.: 10/131,973

(22) Filed: Apr. 24, 2002

(65) Prior Publication Data

US 2002/0177761 A1 Nov. 28, 2002

Related U.S. Application Data

(60) Provisional application No. 60/286,822, filed on Apr. 26, 2001.

(51) Int. Cl.[7] .................................................. A61B 5/00
(52) U.S. Cl. ........................ 600/583; 600/310; 600/345; 29/428; 264/239
(58) Field of Search ................................ 600/309, 310, 600/341, 345, 347, 573, 576, 583, 584; 29/428; 264/239, 328.1

(56) References Cited

U.S. PATENT DOCUMENTS

| | | | |
|---|---|---|---|
| 4,637,403 A | * | 1/1987 | Garcia et al. ............... 600/583 |
| 4,873,993 A | | 10/1989 | Meserol et al. |
| 4,833,068 A | | 11/1989 | Dechow |
| 5,029,583 A | | 7/1991 | Meserol et al. |
| 5,801,057 A | * | 9/1998 | Smart et al. ................ 600/309 |
| 5,951,492 A | | 9/1999 | Douglas et al. |
| D424,696 S | | 5/2000 | Ray et al. |
| D426,638 S | | 6/2000 | Ray et al. |
| D427,312 S | | 6/2000 | Douglas |
| 6,071,251 A | * | 6/2000 | Cunningham et al. ...... 600/584 |
| 6,099,484 A | | 8/2000 | Douglas et al. |
| 6,120,676 A | | 9/2000 | Heller et al. |
| 6,183,489 B1 | | 2/2001 | Douglas et al. |
| 6,315,738 B1 | * | 11/2001 | Nishikawa et al. ......... 600/583 |
| 6,349,229 B1 | * | 2/2002 | Watanabe et al. ........... 600/583 |
| 6,352,514 B1 | | 3/2002 | Douglas et al. |
| 6,620,112 B2 | * | 9/2003 | Klitmose .................... 600/583 |

* cited by examiner

Primary Examiner—Eric F. Winakur
(74) Attorney, Agent, or Firm—Townsend and Townsend and Crew LLP

(57) ABSTRACT

This invention provides for an integrated device having a lance and analytic device in a single disposable unit where the lance releases fluid from skin and the analytic device collects and analyzes the fluid without the user removing an instrument housing which holds the disposable unit. In addition to the device, this invention provides for methods of using and manufacturing the device.

52 Claims, 4 Drawing Sheets

INTEGRATED LANCING AND ANALYTIC DEVICE

CROSS-REFERENCES TO RELATED APPLICATIONS

[Not Applicable]

STATEMENT AS TO RIGHTS TO INVENTIONS MADE UNDER FEDERALLY SPONSORED RESEARCH AND DEVELOPMENT

[Not Applicable]

BACKGROUND OF THE INVENTION

1. Field of the Invention

This invention provides for an integrated device having a lance and analytic device in a single disposable unit where the lance releases fluid from skin and the analytic device collects and analyzes the fluid without the user removing an instrument housing which holds the disposable unit. In addition to the device, this invention provides for methods of using and manufacturing the device.

2. Description of Prior Art

The art of body fluid sampling is inundated with a wide variety of sampling methods and instruments. By traditional methods, in order to perform analysis on biological fluid, a patient is required to make a trip to their physician's office and donate a sample. This is usually in the form of a blood or urine sample that is subsequently delivered to a laboratory and eventually analyzed. In order to obtain the blood sample, it is most common for a hypodermic to be inserted into a vein to gather a large volume of blood, the majority of which is not used in most cases. More recently, blood tests and analyzers have been developed which require the pricking of a finger to supply a drop of blood, which is analyzed by a separate unit.

In recent years there has been a growing need to provide the ability to perform body fluid analysis on the spot, without sending an individual to a physicians office, and a fluid sample to a lab for analysis. Law enforcement and military have pressing needs to be able to perform on the spot testing for drugs of abuse and exposure to CBR (chemical biological and radiological) warfare. Furthermore, in order to enhance the quality of life and for proper management of health, there has been a push to equip the common individual to perform biological fluid testing at home or during normal day-to-day routines without having to visit their physician. Several types of instruments have been developed along the lines of home pregnancy testers, hemoglobin testers, and blood glucose testers for diabetics.

Diabetes mellitus is a chronic disease that affects more than 15 million Americans. About seventy five percent of these are type 2 (non-insulin dependent). Accurate blood glucose monitoring is required for proper management of blood sugar levels for diabetics. Several systems have been developed over the recent years permitting home testing of blood sugar levels. Most of these systems require the user to draw a blood sample usually from the fingertip and deliver the blood sample to a collection device in the form of a capillary and reservoir with predisposed reagents for analysis. Due the sensitivity of the fingertips however, testing is quite painful and even traumatic for many users, especially among children and infants. Recently devices have been developed which sample body fluid from the forearm as a means of drawing body fluid painlessly, U.S. Pat. Nos. D0427312, 06,120,676, D0426,638, D0424,696. However, obtaining the volume of blood required for these systems from the forearm has been difficult.

The art of body fluid sampling is inundated with a variety of instruments and sampling devices, available in a large range of designs. Integration of the skin-penetrating member with the fluid collecting and analyzing portion of body fluid analyzers is uncommon in the industry. Most body fluid analyzing instruments come in two different parts: a skin penetrating instrument, and a collection and analysis instrument. This is a prevalent shortcoming of the current art, the methods and instruments designed for body fluid sampling require two distinctly different steps: a lancing step and a filling step, which requires manual delivery of a relatively large volume of body fluid to the collection device. The proper delivery of the blood to the collection device often requires a good deal of dexterity and is quite difficult for older diabetics, and individuals with failing eyesight. Often the blood drop ends up smeared along the test collection device or on the user, creating a mess and a failed test. As a result tests often need to be repeated several times until the procedure is performed properly.

A device that integrates the skin penetrating and fluid collecting procedures has many advantages. Integrated systems do not require as large as a volume of body fluid to be produced as required for non-integrated systems. This is because integrated systems may be used in a more automated system, eliminating the patient as the fluid delivery mechanism. Integrated and automated systems may demonstrate a high level of precision in collecting the sample, allowing for smaller sample sizes to be generated. Smaller sample sizes result in smaller lancet sizes, less pain and trauma for the user, and fewer if any failed tests.

Several companies and individuals have developed various devices in an attempt to integrate the sample production and collection devices and automate the process. However, there are few, if any, truly integrated skin penetrating and collecting devices currently available.

One such device described by Smart and Subramanian, U.S. Pat. No. 5,801,057, refers to a silicon microsampler. The silicon microsampler is a microchamber forming a cuvette with an integrated hollow silicon needle. The microchamber and needle are formed from one silicon substrate through a series of etching processes. The microchamber and microneedle of the microsampler are covered with a glass layer that is anodically bonded to the silicon portion. The microsampler is filled by inserting the microneedle into the skin; under the skin surface, the microneedle contacts a blood sample and draws it into the microcuvette for analysis.

U.S. Pat. No. 4,873,993, Cuvette, assigned to Personal Diagnostics Inc., describes "a cuvette with or without a lancet secured thereto and extending therefrom for producing skin puncture to produce body fluid of interest, the cuvette is made of optically transparent material and is provided with a shape and a plurality of optical elements such as integrally formed optical elements for causing a light beam to pass therethrough by total internal reflectance and for causing the beam of light to be reflected back along a line different from the direction of the line of entry of the beam of light into the cuvette such as back along a line generally parallel to the line of entry of the beam of light into the cuvette and in the opposite direction to the direction of entry of the beam of light into the cuvette." This device is used with an instrument that performs the lancing operation, U.S. Pat. No. 5,029,583. However, the lance and cuvette are not attached in such a way to facilitate automated filling of the cuvette. The cuvette filled manually by the patient "wiping" the body fluid sample across the opening to the cuvette.

Another device described by Garcia et al., U.S. Pat. No. 4,637,403, refers to a hand-held portable medical diagnostic device. The system utilizes a "disposable needle or lance probe package which carries a chemical reagent strip." The disposable is used within an instrument utilizing "a spring arrangement for actuating a needle or lance into the skin for transferring blood from a finger or other area to the chemical reagent strip." The instrument and actuation system may also create a vacuum at the lance site to help move blood from the wound to the test strip.

Another application described by Douglas et al., U.S. Pat. No. 6,099,484, refers to methods and apparatus for sampling and analyzing body fluid. The device described is an instrument containing a lancet for making an incision, a capillary tube for drawing up fluid, and a test strip affixed to the capillary tube. Various embodiments of the instrument and invention are described. The instrument contains all components mentioned and contains an actuating system that lances and places the capillary at the lance site. Another embodiment describes the instrument first placing a test strip at the skin surface and then piercing the skin through the test strip with a lancet.

Another device by Douglas et al. U.S. Pat. No. 6,183,489 describes a macro collection device where the fluids are drawn up by a capillary tube to an external analytic test strip.

Another device described by Frederick L. Dechow, U.S. Pat. No. 4,883,068, refers to a blood sampling device and method. The instrument consists of a double-sided cannula and a reservoir with a penetrable end cap axially aligned in a compressible device. The device is laid upon the skin and compressed. This motion causes the cannula to first puncture the skin surface and then the reservoir end cap. In this position blood is then delivered to the reservoir.

SUMMARY OF THE INVENTION

The present invention is an integrated lancing and analytic device for collecting fluid from skin. The device has a lance and an analytic device integrated into a single device body. The lance and inlet of the analytic device are positioned in the device body so that the fluid released by the lance is taken up into the inlet by having the device body direct the lance and the analytic device to the fluid released from the skin. The device body is preferably plastic and is fabricated using plastic injection molding.

More specifically the invention comprises an integrated lancing and analytic device for collecting fluid from skin said device having a lance and an analytic device integrated into a single device body wherein: (i.) the lance has a tapered skin penetrating portion extendible from the body so that it penetrates the skin to release fluid when the body of the device is held to the skin; (ii.) the analytic device comprises an inlet, an analytic region having capillary dimensions, an outlet and a signal pathway wherein the analytic region is positioned in fluid communication between the inlet and outlet and the signal pathway transmits a signal of analysis from the analytic region to the outside, optionally the signal is not visible to a user; and (iii.) wherein the lance and inlet of the analytic device are positioned in the device body at an angle of less than 180 degrees so that the fluid released by the lance is taken up into the inlet by having the device body direct the inlet of the lance and the analytic device to approximately the same position thereby collecting the fluid released from the skin.

The lance is an object used to penetrate the skin, less than 2 mm in depth, preferably having the form of a needle. In one embodiment the lance may be rigidly attached to the device body, having a tapered skin-penetrating portion extending from the body. In this embodiment the lance may incorporate a fluid channel, internally such as in a hypodermic syringe, or on the surface. In another embodiment the lance is moveably positioned within a pathway within the body and has a tapered skin-penetrating portion that extends from the body. The lance may be spring loaded in the device body to provide a driving mechanism. The lance is slidably mounted and able to move along the pathway so that it penetrates the skin and retracts to release fluid from the skin when the body of the device is held to the skin. The lance may be fabricated from metal, silicon, or plastic.

The analytic device is used to pull body fluid off from the skin surface and perform an analysis on the fluid. The fluid may be blood, interstitial fluid, or a combination of both, having a volume range of 50–300 nanoliters. The analytic device comprises an inlet, an analytic region, an outlet and a signal pathway wherein the analytic region is positioned in fluid communication between the inlet and outlet and the signal pathway transmits a signal of analysis from the analytic region to the outside. The signal pathway may be either a pair of electrodes or an optical signal. The analytic device may be either held rigidly in the device body or moveably positioned (slidably mounted) within a pathway within the device body. When positioned moveably within the device body the analytic device may be spring loaded within the device body. In one embodiment the device body may create a fluid seal with the analytic device. The analytic device may be fabricated from either silicon, or a combination of silicon with plastic or glass.

One object of the present invention is to provide an instrument system comprising an instrument housing containing an integrated lancing and analytic device for collecting fluid from skin. The instrument housing is fitted to removably house the device having a lance and an analytic device integrated into a single device body. The lance has a tapered skin-penetrating portion which extends from the body so that it penetrates the skin and retracts to release fluid from the skin when the instrument housing is held to the skin; the analytic device comprises an inlet, an analytic region, an outlet and a signal pathway wherein the analytic region is positioned in fluid communication between the inlet and outlet and the signal pathway transmits a signal of analysis from the analytic region to the outside; and the lance and inlet of the analytic device are positioned in the device body so that the fluid released by the lance is taken up into the inlet without removing the instrument housing from the skin. Both the lance and the analytic device may be rigidly attached to the device body, moveable within the device body, spring loaded within the device body, spring loaded within the instrument housing, or driven by an electromechanical device within the instrument housing.

Another object of the present invention is to provide a method of collecting and analyzing fluids from skin. The method comprises four steps: (1) positioning on the skin of an animal an instrument housing containing a removable, integrated lancing and analytic device for collecting fluid from skin said device having a lance and an analytic device integrated into a single device body; (2) penetrating the lance into the skin to release fluid; (3) positioning the analytic device to the location on the skin penetrated by the lance; (4) analyzing the fluid that enters the analytic device through the inlet.

One variation of the method may allow for the lance to be reinserted into the skin while positioning the analytic device on the skin. Another variation of the method may allow for pivoting the device body to position the lance and analytic device on the skin. The fluid in the analytic device may be analyzed using several methods: optical, electrochemical, fluorescence, or chemiluminescence. The preferred analyte for the fluid is glucose.

Another object of the present invention is to provide a process for manufacturing an integrated lancing and analytic device for collecting fluid from skin, the device having a lance and an analytic device integrated into a single device body. The process comprises attaching a lance and analytic device to a device body wherein the lance and inlet of the analytic device are positioned in the device body so that fluid released by the lance is taken up into the inlet without having to remove the device from the skin. This is accomplished by directing the lance and the analytic device to the same position on the skin. By same position, it is meant that the inlet of the analytic device is positioned in adequate proximity to the fluid released by the lance to permit uptake of the fluid without the user having to remove the device from the skin and visibly reposition the inlet to the fluid. This would include a slight rocking motion of the device as in a pivoted configuration.

Unless otherwise stated, all physical variations of the devices described herein are applicable to the methods of manufacturing and methods of uses described herein.

DETAILED DESCRIPTION OF THE INVENTION

Figure 1:
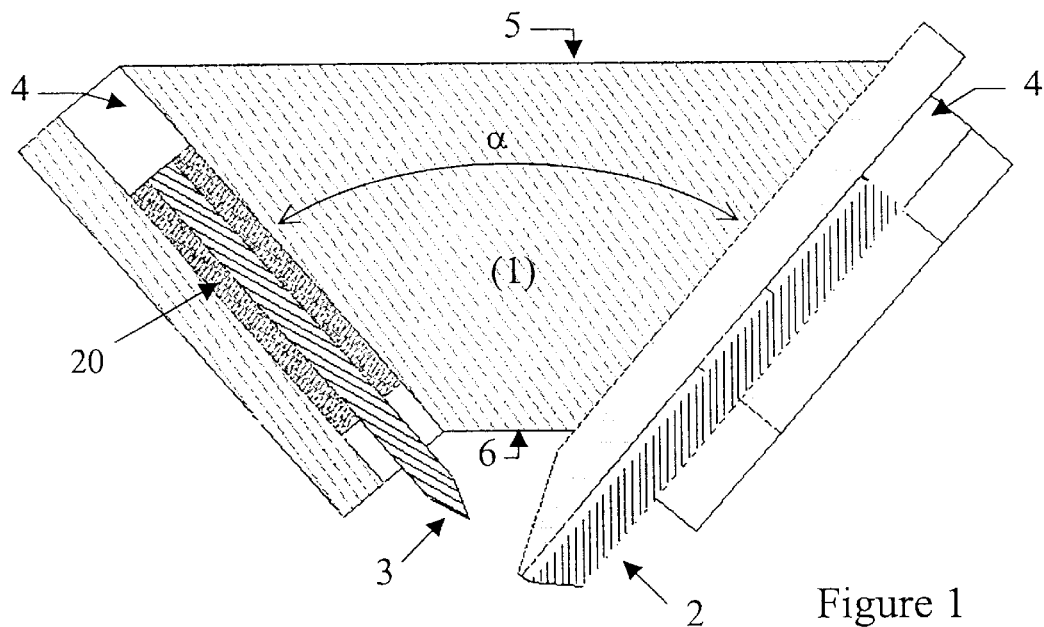
FIG. 1 is a cross sectional side view of the device body, analytic device and lance where the analytic device and lance are moveable within the device body.

The present invention is an integrated lancing and analytic device for collecting body fluid from skin said device having a lance (3) and an analytic device (2) integrated into a single device body (1). The preferred material of the device body (1) is plastic and is fabricated from plastic injection molding. The device body (1) may vary in size and shape depending on the specific design. When the device body (1) is of the form shown in FIG. 1 the lance (3) and analytic device (2) are positioned moveably along pathways (4) within the device body (1). When the device body (1) is of this general design, the device body (1) may vary in size from 20 mm–5 mm at the distal end (5) (preferred 10 mm), 10 mm to 1 mm at the proximal end (6) (preferred 2.5 mm), and 5 mm–10 mm thick (preferred 7.5 mm). The pathways (4) may be in the form of slots within the device body (1). In this embodiment the slots may vary in size from 3–5 mm wide and 1–5 mm deep. The preferred dimensions are such that the lance (3) and analytic device (2) are able to tightly fit within the slots without impairing motion along the pathways (4).

When the general design of the device body (1) is of the form shown in FIGS. 4–9, the lance (3) and analytic device (2) are held rigidly within the device body (1). When the device body (1) is of the form shown in FIGS. 4–8, the device body (1) may range in size from 3 mm–8 mm in length, 1 mm–5 mm wide at the distal end (5), 50 $\mu$m–5 mm wide at the proximal end (6), and 500 $\mu$m–3 mm thick. The preferred dimensions are 3 mm long, 2 mm wide at the distal end (5), 50 $\mu$m wide at the proximal end (6), and 1.5 mm thick. In this general design the device body (1) may have a slot (7) that rigidly holds the analytic device (2). The preferred dimensions of the slot (7) are such that the slot (7) is slightly smaller than the analytic device (2) such that the analytic device (2) is held rigidly in an interference fit. When the device body (1) is of the general design shown in FIG. 9, the device body (1) may have the same general size as the embodiment described in FIG. 1. In the embodiment shown in FIG. 9 the device body (1) may have a pivot (21). A pivot is a cylinder, flexible element or rocking point upon which a rotational or rocking motion is possible. The pivot may be a part of the device body or the housing with a diameter ranging from 1 mm to 5 mm. The preferred diameter is 2 mm. A reciprocal feature designed to mate with the pivot point is created on element not having the pivot.

The lance (3), as shown in FIGS. 1, 4–9, comprises a tapered skin-penetrating portion that extends from the device body (1) so that it penetrates and releases fluid from the skin when the device body (1) is held to the skin. The lance (3) protrudes from the device body (1) 0.5 mm–3 mm. The preferred protrusion distance is 1.5 mm. The lance (3) may have a diameter ranging from 100 $\mu$m to 400 $\mu$m. The preferred diameter is 200 $\mu$m. The lance (3) may be formed from metal, silicon, or glass. The preferred material is metal. The lance (3) may have a hollow bore or channel in the interior or along the outer surface. The bore in the lance interior may range in diameter from 10 $\mu$m to 20 $\mu$m. The preferred diameter is 15 $\mu$m. The channel on the lance surface may range in size from 25 $\mu$m–5 $\mu$m wide and 50–5 $\mu$m deep. The preferred dimensions of the channel are 10 $\mu$m×10 $\mu$m.

The analytic device (2), as shown in FIGS. 1–9, comprises an inlet (8), an analytic region (9), an outlet (10) and a signal pathway (11) wherein the analytic region (9) is positioned in fluid communication between the inlet (8) and outlet (10) and the signal pathway (11) transmits a signal of analysis from the analytic region (9) to the outside. The inlet (8) is 15 $\mu$m–200 $\mu$m wide. The analytic region (9) is dimensionally sized to permit and have capillary properties. This means that the analytic region has dimensions that permit uptake of body fluids by capillary action. These dimensions include 500 $\mu$m–2 mm wide and 20 $\mu$m–150 $\mu$m deep with a volume of 50 nl–300 nl, the outlet (10) is 100 $\mu$m–500 $\mu$m wide. The preferred dimensions are 30 $\mu$m wide at the fluid inlet (8), 1 mm wide and 50 $\mu$m deep with a volume of 100 nl at the analytic region (9), and 200 $\mu$m wide at the outlet (10). The analytic device (2) may range in size from 3 mm–8 mm in length, 1 mm–5 mm wide at the distal end (12), 50 $\mu$m–5 mm wide at the proximal end (13), and 100 $\mu$m–3 mm thick. The preferred dimensions are 3 mm long, 2 mm wide at the distal end (12), 50 $\mu$m wide at the proximal end (13), and 500 $\mu$m thick. The analytic device (2) may be fabricated from silicon or plastic, the preferred material is silicon. The analytic device (2) may protrude from the device body (1) 1 mm–3 mm. It is preferred that the analytic device (2) protrudes from the device body (1) 1.5 mm.

EXAMPLES

The following examples are provided by way of illustration only and not by way of limitation. Those of skill will readily recognize a variety of noncritical parameters which could be changed or modified to yield essentially similar results.

The integrated lancing and analytic device exists in several embodiments. In summary, the device of the present invention combines both a lance and analytic device in such a way that they may be used together conveniently for lancing a skin surface and drawing a small sample of body fluid. In all embodiments of the invention the lance and analytic device are combined together, integrated in a device body. They may be held rigidly in the device body or allowed to move relative to each other within the device body.

Example 1

The device body is the housing for the lance and analytic device. The device body holds and positions both the lance and analytic device at the proper location with respect to each other. The device body is preferably plastic and fabricated from plastic injection molding. As seen in FIG. 1, in one embodiment of the invention the lance (3) and analytic device (2) may be mounted within the device body (1) in such a manner that either or both the lance (3) and the analytic device (2) are capable of moving within the device body (1) and relative to each other. The lance (3) and inlet (8) of the analytic device (2) are positioned in the device body (1) so that the fluid released by the lance (3) is taken up into the inlet (8) by having the device body (1) direct the lance (3) and the analytic device (2) to the fluid released from the skin. In this embodiment either or both the lance (3) and the analytic device (2) may move linearly along pathways (4) within the device body (1). The pathways (4) are guiding elements such as grooves, slots, or rails within the device body (1). Grooves and slots may be formed during the plastic injection molding process; rails may be fabricated from metal and inserted after the molding process. The pathways (4) are oriented such that the fluid released by the lance (3) is taken up into the inlet (8) by having the device body (1) direct the lance (3) and the analytic device (2) to the fluid released from the skin.

The analytic device and lance are positioned at an angle of less than 180° relative to each other (alpha, □). This angle permits the analytic device to be placed in the proximate location of the skin where the lance has released fluid.

The driving force for the lance (3) and analytic device (2) within the device body (1) may be provided by a spring or an electromechanical actuation mechanism such as a motor or solenoid located in an accompanying instrument housing. The instrument housing is a plastic injection molded casing, preferably hand held. The device body (1) is intended for use with the instrument housing. The instrument housing contains the actuation mechanism that interacts with the device body (1) and drives the lance (3) and analytic device (2). The preferred method of actuation is spring loading. Either or both the lance (3) and analytic device (2) may be spring-loaded within the device body (1) to facilitate linear motion and to provide an actuation method. The spring-loaded component is attached to a spring or combination of springs to provide movement. The spring configuration may include an actuation spring and a bounce-back spring, as well as a coking and release mechanism. Similar spring loaded devices are commonly manually cocked and actuated by the use of a pull lever and a push button integrated into the instrument housing.

Figure 2:
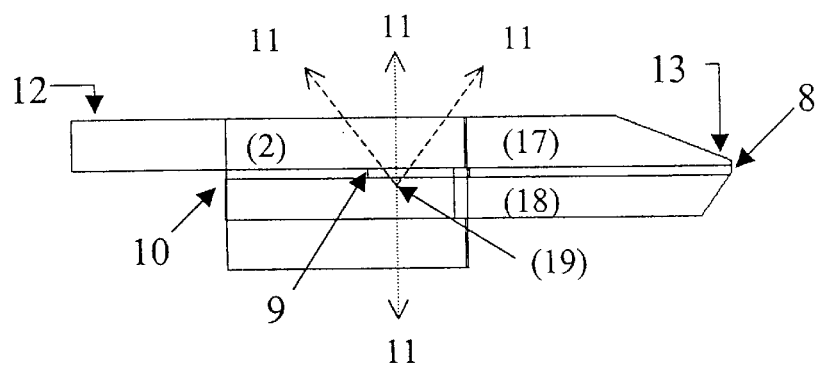
FIG. 2 is a side view of the analytic device.

In this embodiment the analytic device (2) is allowed to move within the device body (1). The analytic device (2) is a device for collecting and analyzing body fluid. The analytic device (2) may be fabricated from silicon, plastic, glass or any combination of the three. The preferred material is single crystal silicon with a (100) crystallographic orientation; however, polysilicon or other crystallographic orientations may be used. The analytic device (2) may be formed in silicon using standard semiconductor processing techniques. These consist primarily of spin coating photoresist on a silicon wafer, exposing the photoresist to UV light with a protective mask defining the desired etching pattern, and etching the silicon, removing silicon from selected areas to form the analytic device (2). The preferred etching method is using a high rate plasma etcher, however, KOH (potassium hydroxide) may be used. Referring to FIG. 2, the analytic device (2) comprises an inlet (8), an analytic region (9), an outlet (10) and a signal pathway (11). The analytic region (9) is in fluid communication with the inlet (8) and outlet (10) and the signal pathway (11) transmits a signal of analysis from the analytic region (9) to the outside.

The signal pathway (11) and signal of analysis are means of communicating the analysis within the analytic region (9) to the outside. The signal pathway (11) may be along electrodes (14) within the analytic device (2) when used in an electrochemical application or through the analytic device (2) when used in an optical application. Similarly, the signal of analysis is either an electrical or optical signal that communicates the results of the analysis within the analytic region (9) of the analytic device (2) to the outside. An advantage of the system is that the signal is not directly read by the user which can result in user error as with a test strip located outside the capillary portion of the system. Rather the signal is read indirectly by a photosensitive device e.g., a photodiode or a device that reads electrical potential or current. This conveys sensitivity and reproducibility to the system.

Figure 3:
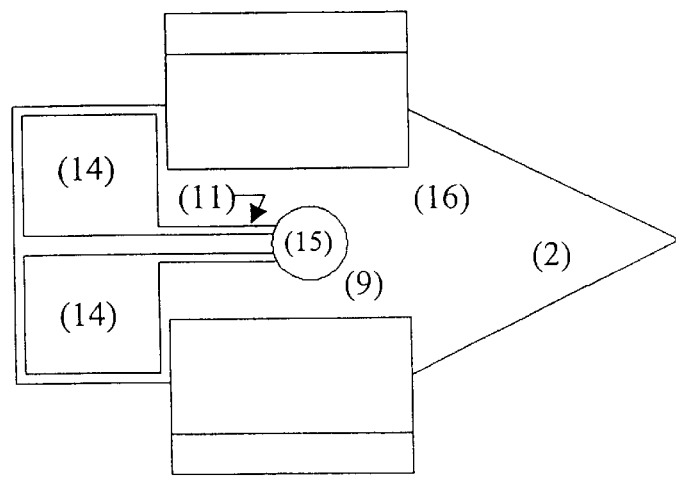
FIG. 3 is a top view of the inner surface of one portion of the analytic device.

When measured electrically, as shown in FIG. 3, an electrochemical sensor (15) may be pre-deposited on an inner surface (16) of the analytic device (2) in the analytic region (9). The electrochemical sensor (15), when used for glucose measurement, is based on the fact that the enzyme glucose oxidase catalyses the oxidation of glucose to gluconic acid. The first generation glucose biosensors used molecular oxygen as the oxidizing agent. Commercially available finger stick glucose devices use a ferrocene based mediator system in lieu of molecular oxygen. Recently, immobilization techniques have been developed to "wire" an enzyme directly to an electrode, facilitating rapid electron transfer and hence high current densities.

In an electrochemical system the electrodes (14) act as a signal pathway (11) for communicating the results of the electrochemical reaction from the electrochemical sensor (15) between the analytic region (9) and the exterior of the analytic device (2). The electrodes (14), as shown in FIG. 3, are conducting traces deposited on the inner surface (16) of the analytic device (2) and in contact with the electrochemical sensor (15). The electrodes (14) may be made from any noble metal: primarily gold, platinum or silver. The metal electrodes (14) can be deposited on the analytic device (2) by either by sputtering or by evaporation in a vacuum chamber. Sputtering is the preferred method of deposition of metals. The metal deposited substrate will be coated with a thin layer of photoresist. The photoresist will then be exposed and patterned with exposure to UV light. The metal can then be etched with a reagent to create the specific metal trace patterns. In an electrochemical system the electrical signal conducted via the electrode signal pathway (11) is analyzed using an accompanying instrument housing.

In another embodiment of the present invention the signal pathway (11) and the signal of analysis may be optical. In this embodiment the chemical reaction inside the analytic device (2) is read using either optical transmittance or optical reflectance methods. When used in an optical analysis system the analytic device (2) may have reagents deposited on the inner surface (16) in the analytic region (9). The reagents react with analytes in the body fluid, such as glucose or hemoglobin, to form a color change. In an optical system the signal source is a light emitting diode (LED) or a diode laser of appropriate wavelength. The preferred wavelength range is 600 nm–650 nm when the analyte is glucose. A secondary LED or diode laser may be used in the wavelength region of 700 nm–800 nm for background absorbance compensation. The optical signal is analyzed using an optical sensor present in an accompanying instrument housing.

Referring to FIG. 2, in a reflectance system the signal pathway (11) is in through one member (17) of the analytic device (2) to the analytic region (9), through the body fluid present in the analytic region (9) to the surface (19) of the analytic region (9), off of the surface (19) of the analytic region (9) and out through the same path in reverse order. In a transmittance system the signal pathway (11) is in through one member (17) of the analytic device (2) to the analytic region (9), through the body fluid present in the analytic region (9), and out through the opposing member (18) of the analytic device (2). Other embodiments may incorporate the device body (1) into the signal pathway.

Another advantage of this invention is that the analytes are read within the capillary dimensions of the analytic region of the analytic device. This affords economy of manufacture over the prior art devices.

Referring to FIG. 1, in the present embodiment the lance (3) is allowed to move within the device body (1). The lance (3) is a device for penetrating the skin to a depth sufficient to induce body fluid to well up to the skin surface. The lance (3) is tapered at one end, coming to a point with sufficient sharpness for penetrating skin, breaking the surface with minimal required damage to skin tissue. The lance (3) is preferably fabricated from metal but may also be fabricated from silicon or plastic. In the preferred embodiment the lance (3) is a metal needle, protruding cylindrically from the front of the device body (1) with one end tapered to a point. In an alternative embodiment the lance (3) may be metal having the shape of a razor edge. The lance (3) protrudes from the front of the device body (1) in an orientation such that when the device body (1) is held to the surface of the skin the lance (3) penetrates the skin surface. In this embodiment, shown in FIG. 1, the lance (3) is imbedded into a lance body (20) that is positioned in the pathway (4) of the device body (1). The lance body (20) is plastic and is fabricated from plastic injection molding. The lance (3) may be molded into the lance body (20) or embedded into the lance body (20) by heating and inserting the lance (3) under high pressure into the lance body (20) after the lance body (20) has been fabricated.

Another embodiment of the lance (3) includes fabricating it from silicon. Doped or non-doped silicon may be used. It is preferred to use (100) oriented single crystal silicon. However, polysilicon or other crystallographic orientations may be used. In this embodiment the silicon lance (3) may have the shape of a needle tapering to a point with sufficient sharpness for penetrating skin. The silicon lance (3) may be attached to and protrude from the lance body (20) in the same manner as described for the metal lance (3) above. Silicon needles may be fabricated using processing steps common in the semiconductor processing industry. These steps include spin coating photoresist on a silicon wafer, UV exposing and patterning the needle geometry into the photoresist, and etching the wafer in plasma or potassium hydroxide (KOH), thus removing silicon from selected areas to form silicon needles. The preferred method is to use high rate plasma etching. The steps for plasma etching are well established and known to those experienced in the art.

In yet another embodiment the lance (3) may be formed out of plastic. In this embodiment the lance (3) would be formed as part of the lance body (20) during the plastic injection molding process and protrude from the front of the lance body (20). The plastic lance (3) would be tapered as previously described to have sharpness sufficient for penetrating the skin surface.

Example 2

Figure 7:
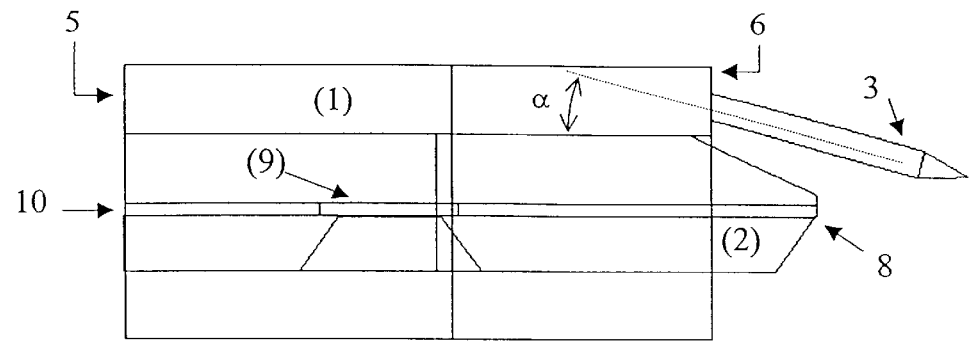
FIG. 7 is a side view of the device body, analytic device and lance.
Figure 8:
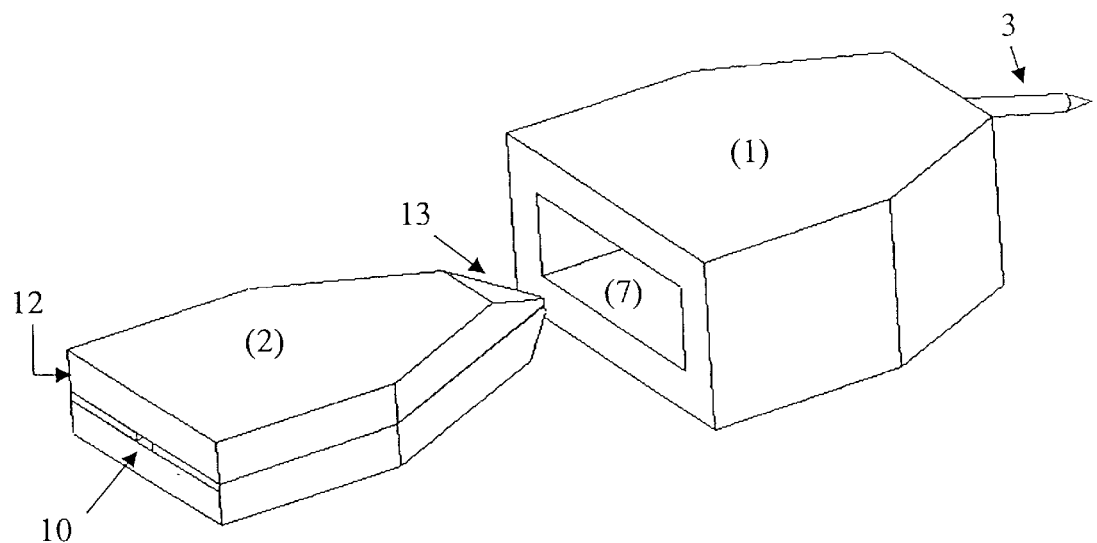
FIG. 8 is an exploded perspective view of the device body, analytic device and lance.
Figure 9:
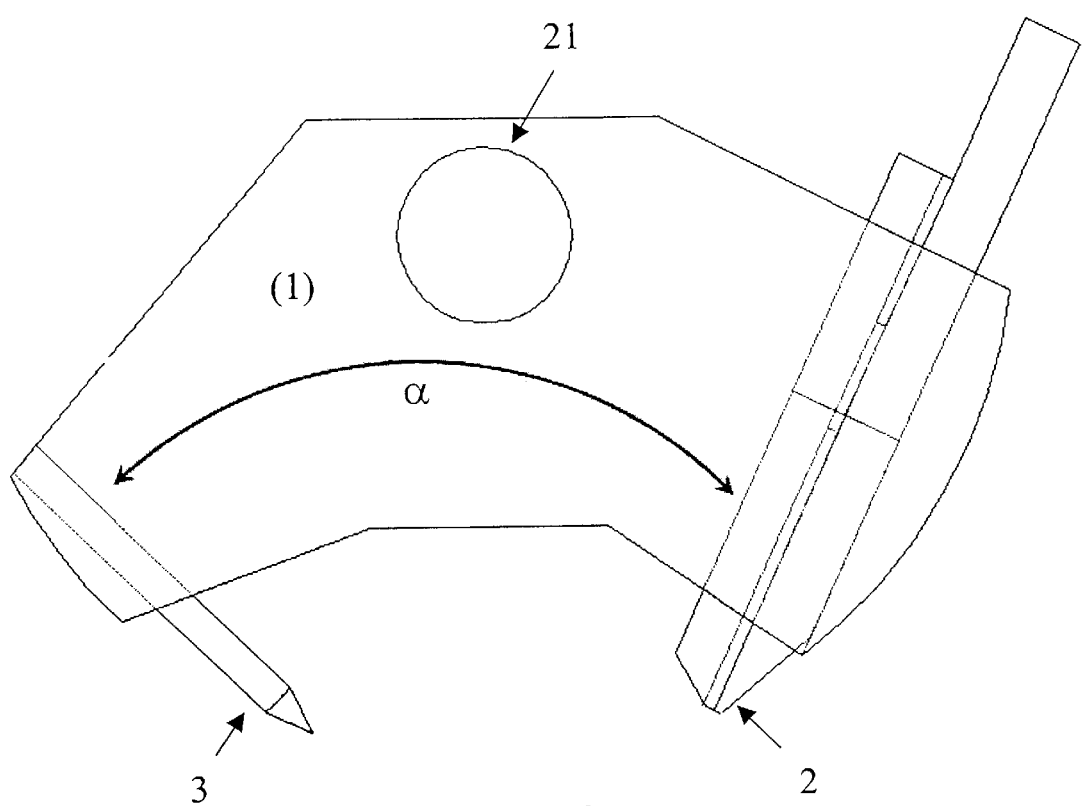
FIG. 9 is a side view of the device body, analytic device and lance where the analytic device and lance are imbedded rigidly in the device body and the device body has a pivot point.

In an alternative design of the invention, as seen in FIGS. 4–9, the device body (1) may hold the lance (3) and analytic device (2) rigidly, immobile with respect to the device body (1) and each other. As described in example 1, the device is intended for use within an instrument system. The instrument system comprises an instrument housing containing the integrated lancing and analytic device for collecting fluid from skin. The instrument housing is fitted to removably house the device, said device having a lance (3) and an analytic device (2) integrated into a single device body (1) wherein the lance (3) and inlet (8) of the analytic device (2) are positioned in the device body (1) so that the fluid released by the lance (3) is taken up into the inlet (8) without removing the instrument housing from the skin. The preferred material for the device body (1) is plastic; the device body (1) is fabricated from plastic injection molding. The lance (3) and analytic device (2) are positioned within the device body (1) such that an appropriate motion of the device body (1) directs the lance (3) and the analytic device (2) to the fluid released from the skin. This position is represented by the angle alpha (□) in FIGS. 1, 4, 7 and 9. The angle alpha is less than 180 degrees and is preferably less than 75 degrees and most preferably between 90 and 25 degrees. The appropriate motion may be either linear or radial within the instrument housing and controlled using either a spring or an electromechanical actuator such as a motor or solenoid. The device body (1) may include a connecting feature, enabling itself to be connected with the actuator. For the case of radial motion, as seen in FIG. 9, the device body (1) may include a pivot point (21) that may be formed as a hole or a hinge in the device body (1) during the plastic injection molding.

In this embodiment the analytic device (2), as seen in FIGS. 4–9, is attached rigidly to the device body (1). The analytic device (2) is a device for collecting and analyzing body fluid. The analytic device (2) comprises an inlet (8), an analytic region (9), an outlet (10) and a signal pathway (11), as previously described in example 1. The analytic region (9) is in fluid communication with the inlet (8) and outlet (10) and the signal pathway (11) transmits a signal of analysis from the analytic region (9) to the outside. The signal pathway (11) and signal of analysis are either an optical or electrical consistent with the description provided in example 1. The analytic device (2) may be fabricated from silicon, plastic, glass or any combination of the three. The preferred material is silicon. The analytic device (2) may be formed in silicon using the standard semiconductor processing techniques described in example 1.

Figure 4:
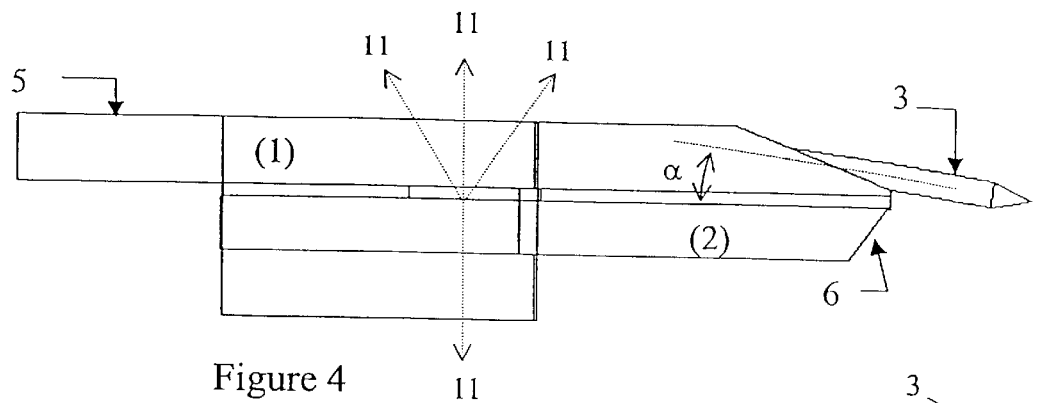
FIG. 4 is side view of the device body, analytic device and lance where the analytic device and lance are imbedded rigidly in the device body.
Figure 5:
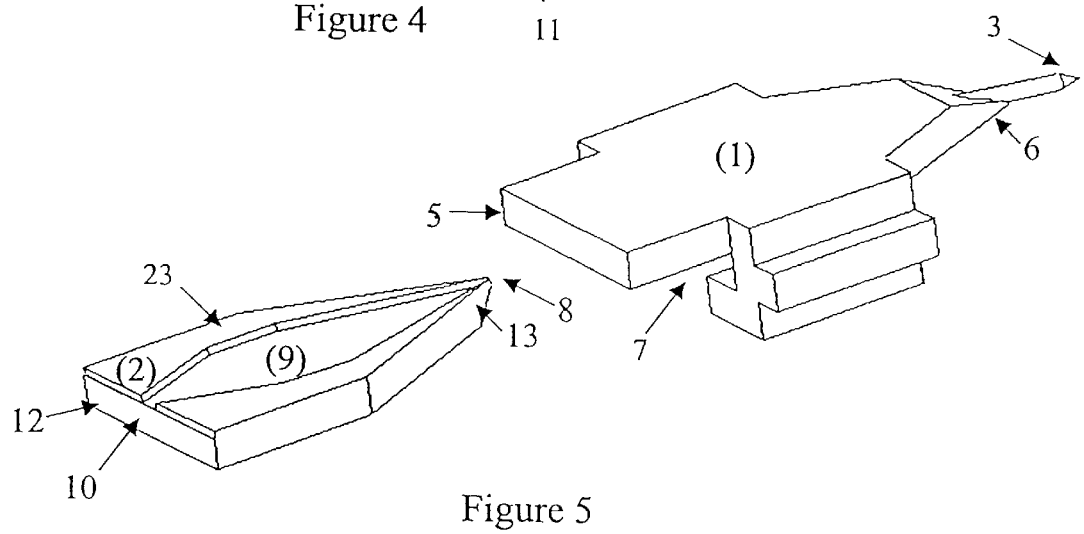
FIG. 5 is an exploded perspective view of the device body, analytic device and lance.
Figure 6:
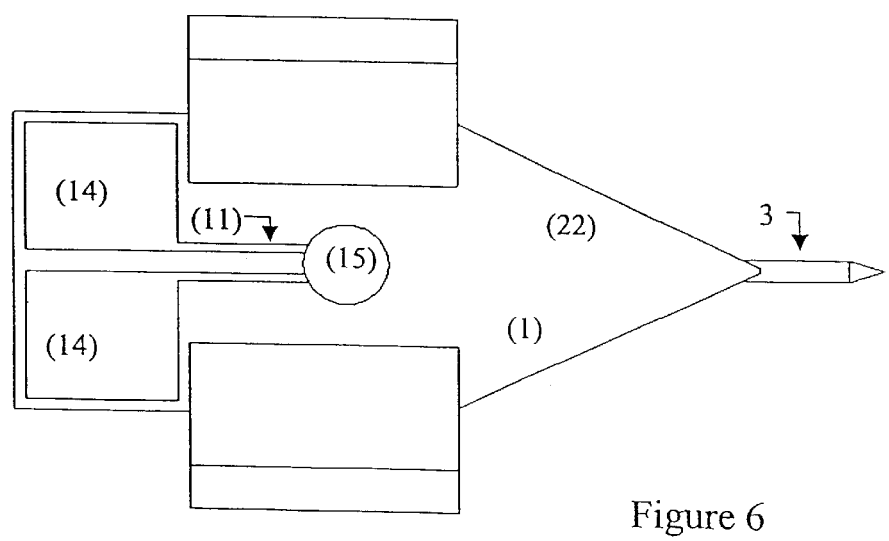
FIG. 6 is a top view of the inner surface of the device body with electrochemical sensor and electrodes.

In one embodiment of the present invention, as seen in FIGS. 4–6, the device body (1) may act as a cover for the analytic device (2) providing a fluid seal and replacing either element (17) or (18) of FIG. 2. With the device body (1) sealing the analytic region (9) to form a fluid barrier, there is significant cost savings. In such a design, the inner surface (22) of the device body (1) contacts the surface (23) of the analytic device (2) forming a fluid capillary with a trench in the analytic device (2) creating the ability to direct fluid along the capillary. The seal may be created using mechanical pressure, sonic welding of plastics or adhesives. In this embodiment the device body (1) has a shape similar to the analytic device (2) such that the analytic device (2) fits tightly into the device body (1) forming the fluid seal and held rigidly within.

As seen in FIGS. 4–6, the device body (1) may form part of the signal pathway (11) of the analytic device (2). Body fluid, upon entering the analytic device (2), comes into contact with reagents in the analytic region. Upon contact with the reagents a chemical reaction takes place that may be read via either an electrical or optical signal pathway (11). When measured electrically an electrochemical sensor (15) may be pre-deposited on either the analytic device (2) in the analytic region (9) or on the inner surface (22) of the device body (1) in an area that is located directly over the analytic region (9) of the analytic device (2). Electrodes (14) are deposited in contact with the electrochemical sensor (15) on either the analytic device (2) or the inner surface (22) of the device body (1). The materials and methods for fabricating the electrodes (14) and electrochemical sensor (15) are consistent with those described in example 1.

Referring to FIG. 4, the device body (1) may form part of an optical signal pathway (11) for the analytic device (2). In this embodiment the chemical reaction inside the analytic device (2) is read using either optical transmittance or optical reflectance methods. In these embodiments the device body (1) is formed of an appropriate optically transparent material. The device body (1) will not appreciably block radiation in the desired wavelength range, 600–900 nm. In this embodiment the preferred device body (1) material is plastic, however, glass may alternately be used. When used in an optical analysis system, reagents may be deposited on the analytic device (2) in the analytic region (9) or on the inner surface (22) of the device body (1). The reagents react with analytes in the body fluid, such as glucose or hemoglobin, to form a color change. In this embodiment the specific signal pathway (11) is similar to the descriptions provided in example 1, incorporating the device body (1). Also, in an optical system, an LED or a diode laser, and an optical sensor are provided in an accompanying instrument as described in example 1.

As seen in FIGS. 7–8, in other embodiments of the current invention the device body (1) may hold the analytic device (2) rigidly within the device body (1) but not form the fluid seal with the analytic device (2). Various designs are possible for the design of the device body (1), and are not limited to the representations shown. When the analytic device (2) is held rigidly in the device body (1) and the device body (1) is not used to form a fluid seal with the analytic device (2), the previously mentioned electrochemical sensor, electrodes, and reagents may be deposited within the analytic device (2) itself in a manner consistent with techniques discussed above. Similarly, the signal pathway may vary slightly to include various members of the analytic device (2) and various surfaces of the device body (1) when used in alternate embodiments.

As seen in FIGS. 4–9, the lance (3) may be attached rigidly to the device body (1). The lance (3) has a tapered skin-penetrating portion that extends from the device body (1) so that it penetrates the skin when the body of the device is held to the skin. In this embodiment the lance (3) may have the same design and be fabricated from the same material and processes previously described in example 1. Furthermore, when the lance (3) is attached rigidly to the device body (1), the lance (3) may be attached consistent with methods described in example 1 above, substituting the device body (1) for the lance body (20).

When the lance (3) is attached rigidly to the device body (1) the lance (3) may exist in other embodiments not previously described. The lance (3) may incorporate a fluid channel. The fluid channel is a conduit of appropriate dimensions to cause body fluid to move along the fluid channel due to capillary forces. The channel may be formed inside the lance (3), forming a hollow needle such as a hypodermic syringe, or on the surface of the lance (3) forming an open capillary. In either embodiment the lance (3) protrudes from the front of the device body (1) in an orientation such that when the device body (1) is held to the surface of the skin the lance (3) penetrates the skin surface. The lance (3) may be attached to the device body (1) in a manner consistent with the methods previously described. In either embodiment the channel forms a fluid capillary capable of transporting body fluid from the skin surface to the fluid inlet (8) of the analytic device (2). The lance (3) may be imbedded into the device body (1) at an orientation to the analytic device (2) such that body fluid is delivered from the channel in the lance (3) to the fluid inlet (8) of the analytic device (2). When constructed with a channel the lance (3) may be formed from metal, silicon or plastic. When the lance (3) is fabricated from metal with the channel inside the lance (3) is a hypodermic syringe and is fabricated using common methods. When fabricated from metal and the channel is formed on the surface, the channel may be formed using metal etching techniques. When the lance (3) is fabricated from silicon, the lance (3) and the channel, either internal or on the surface, may be fabricated using silicon processing techniques previously described. When the lance (3) is fabricated from plastic, the lance (3) and the channel, either internal or on the surface, may be formed form insert plastic injection molding.

Methods of Using

This invention is intended to provide a disposable integrated lance and analytic device for use in a one-step collection and analysis of small volumes of body fluid. By a one-step collection method, it is meant that the integrated lancing and analytic device body positions the inlet of the analytic device to the fluid released from the lance without the user visually sighting the fluid and manually bringing the inlet to the fluid.

Body fluids that may be collected and analyzed are blood, interstitial fluid or a mixture of blood with interstitial fluid. The preferred analyte is glucose. Other analytes that may be detected include but are not limited to hemoglobin, sodium, potassium, blood gasses, and drugs of abuse. The present invention provides a device that simplifies the lancing and collection process by integrating the lance and analytic device into a device body. The analytic device may be a nanocuvette, providing a device that is easy to fill using capillary forces. The design of the present invention is well suited for adaptation and use in either optical or electrochemical analysis systems. The invention incorporates a signal pathway into the analytic device and device body for communication of analysis results. The invention is also well suited for use in a hand-held instrument housing containing an actuating, loading, and ejecting system capable of performing the necessary operations, requiring minimal manipulation from the user.

One of the most critical shortcomings of the current art is that the methods and instruments designed for body fluid sampling require two distinctly different steps: a lancing step and a filling step, which requires manual delivery of a relatively large volume of body fluid to the collection device. This two-step manual system is a very inaccurate, painful and messy method of delivering the test fluid to the collection device. Lancets need to be large to draw the required amount of blood. This causes a great deal of pain for the user. A good degree of dexterity is required to accurately deliver the blood to the collection device; as a result sampling is often performed improperly, requiring additional lancing.

In the present invention the lance and analytic device are combined within a device body, and the device body is located within an instrument housing. To gather a body fluid sample, a surface of the instrument housing is brought into contact with the user's skin. Once contact is made between the instrument housing and the skin surface, the actuation system within the instrument housing positions the device body, the lance, and the analytic device. The lance and the inlet of the analytic device are positioned in the device body so that the fluid released by the lance is taken up into the inlet by having the device body direct the lance and the analytic device to the fluid released from the skin without removing the instrument housing from the skin. This procedure facilitates an automatic lancing and sampling method for the collection of body fluid. The positioning is accomplished by providing an angle between the inlet and the lance tip that approximates the contact of the skin at the point of fluid release.

The automatic nature of the present invention provides a device with far greater accuracy in picking up the body fluid sample from the skin surface. As a result, producing a large volume of body fluid on the skin surface is not required for accurate collection of the sample. The greater accuracy of the automatic collection method allows for a much smaller volume of body fluid being produced on the skin surface and a much smaller lance size than commonly used. In the present invention the lance is sized to cause a minimum degree of damage to the skin surface. Furthermore, fabricating a nanocuvette from silicon for use as the analytic device provides a collection device with precisely controlled volume requirements consistent with the small volumes of body fluid being produced from the lance. The overall system results in greater collection accuracy, lower volume requirements from the lance and collection device, smaller lancet sizes, less pain and trauma for the user, and fewer if any failed tests.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An integrated lancing and analytic device for collecting fluid from skin said device having a lance and an analytic device integrated into a single device body wherein:
   i. the lance has a tapered skin penetrating portion extendible from the body so that it penetrates the skin to release fluid when the body of the device is held to the skin;
   ii. the analytic device comprises an inlet, an analytic region having capillary dimensions, an outlet and a signal pathway wherein the analytic region is positioned in fluid communication between the inlet and outlet and the signal pathway transmits a signal of analysis from the analytic region to the outside said signal not visible to a user; and
   iii. wherein the lance and inlet of the analytic device are positioned in the device body at an angle of less than 180 degrees so that the fluid released by the lance is taken up into the inlet by having the device body direct the lance and the analytic device to the fluid released from the skin.

2. A device of claim 1 wherein the device body creates a fluid seal with the analytic device.

3. A device of claim 1 wherein the lance is a needle.

4. A device of claim 1 wherein the analytic device holds 50–300 nanoliters of fluid.

5. A device of claim 1 wherein the signal pathway is a pair of electrodes.

6. A device of claim 1 wherein the signal pathway transmits an optical signal.

7. A device of claim 1 wherein the fluid is blood.

8. A device of claim 1 wherein the fluid is interstitial fluid.

9. A device of claim 1 wherein the analytic device is held rigidly in the device body.

10. A device of claim 1 where in the lance is rigidly fixed to the device body.

11. A device of claim 1 wherein the lance is extendible by its being moveably positioned along a pathway within the device body.

12. A device of claim 1 wherein the lance is spring loaded in the device body.

13. A device of claim 1 wherein the analytic device is moveably positioned within a pathway within the device body to extend to the fluid released on skin.

14. A device of claim 1 wherein the analytic device is spring loaded within the device body.

15. A device of claim 1 wherein the lance penetrates less than 2 mm into the skin.

16. An instrument system comprising an instrument housing containing an integrated lancing and analytic device for collecting fluid from skin said instrument housing fitted to removably house the device said device having a lance and an analytic device integrated into a single device body wherein:
   i. the lance has a tapered skin penetrating portion which extends from the body so that it penetrates the skin and retracts to release fluid from the skin when the instrument housing is held to the skin;
   ii. the analytic device that comprises an inlet, an analytic region, an outlet and a signal pathway wherein the analytic region is of capillary dimension and is positioned in fluid communication between the inlet and outlet and the signal pathway transmits a signal of analysis from the analytic region to the outside said signal not visible to a user; and iii. wherein the lance and inlet of the analytic device are positioned in the device body at an angle of less than 180 degrees so that the fluid released by the lance is taken up into the inlet without removing the instrument housing from the skin.

17. A system of claim 16 wherein the analytic device holds 50–300 nanoliters of fluid.

18. A system of claim 16 wherein the signal pathway is a pair of electrodes.

19. A system of claim 16 wherein the signal pathway transmits an optical signal.

20. A system of claim 16 wherein the lance is a needle.

21. A system of claim 16 wherein the lance is a hypodermic syringe.

22. A system of claim 16 wherein the lance has a fluid channel.

23. A system of claim 16 wherein the lance is rigidly fixed in the device body.

24. A system of claim 16 wherein the lance is spring loaded in the device body.

25. A system of claim 16 wherein the lance is spring loaded in the instrument housing.

26. A system of claim 16 wherein the lance is driven by an electromechanical device in the instrument housing.

27. A system of claim 16 wherein the analytic device is spring loaded in the device body.

28. A system of claim 16 wherein the analytic device is spring loaded in the instrument housing.

29. A system of claim 16 wherein the analytic device is driven by an electromechanical device in the instrument housing.

30. A system of claim 16 wherein the device body pivots in relation to the instrument housing.

31. A system of claim 16 wherein the analytic device is rigidly fixed to the device body.

32. A system of claim 16 having a pivot point mated to a pivot receptacle whereby the device body moves relative to the instrument housing with the pivot point and receptacle positioned opposite each other on the device body and housing.

33. A method of collecting and analyzing fluids from skin said method comprising the steps of:
  a) positioning on the skin of an animal an instrument housing containing a removable, integrated lancing and analytic device for collecting fluid from skin said device having a lance and an analytic device integrated into a single device body wherein:
    i. the lance comprises a tapered skin penetrating portion which extends from the body so that it penetrates and releases fluid from the skin when the body of the device is held to the skin;
    ii. the analytic device comprises an inlet, an analytic region, an outlet and a signal pathway wherein the analytic region is of capillary dimension and is positioned in fluid communication between the inlet and outlet and the signal pathway transmits a signal of analysis from the analytic region to the outside where the signal is not visible to the user; and
    iii. wherein the lance and inlet of the analytic device are positioned in the device body at an angle of less than 180 degrees so that the fluid released by the lance is taken up into the inlet by directing the lance and the analytic device to the fluid without removing the instrument housing from the skin;
  b) penetrating the lance into the skin to release fluid; and
  c) positioning the analytic device to the location on the skin penetrated by the lance; and
  d) analyzing the fluid that enters the analytic device through the inlet.

34. A method of claim 33 wherein the analytic device is held rigidly in the device body.

35. A method of claim 33 wherein the lance can move within the device body.

36. A method of claim 33 wherein the analytic device can move within the device body to extend to the fluid on the skin.

37. A method of claim 33 wherein the lance is held rigidly in the device body at an angle with respect to the analytic device.

38. A method of claim 33 wherein the lance is reinserted into the skin while positioning the analytic device on the skin.

39. A method of claim 33 wherein the device body is pivoted to position the lance and analytic device on the skin.

40. A method of claim 33 wherein the lance and analytic device move within the device body for positioning on the skin.

41. A method of claim 33 wherein the fluid is analyzed optically.

42. A method of claim 33 wherein the fluid is analyzed electrochemically.

43. A method of claim 33 wherein the fluid is analyzed using fluorescence.

44. A method of claim 33 wherein the fluid is analyzed using chemiluminescence.

45. A method of claim 33 wherein the fluid is analyzed for glucose.

46. A process for manufacturing an integrated lancing and analytic device for collecting fluid from skin said device having a lance and an analytic device integrated into a single device body said process comprising attaching a lance and analytic device to a device body wherein the lance and inlet of the analytic device are positioned in the device body so that fluid released by the lance is taken up into the inlet without having to remove the device from the skin, by directing the lance and the analytic device to the same position on the skin,
  wherein the lance has a tapered, skin-penetrating portion configured to extend from the body so that it penetrates and releases fluid from the skin when the body of the device is held to the skin; and,
  wherein the analytic device comprises an inlet, an analytic region, an outlet and a signal pathway wherein the analytic region is of capillary dimension and positioned in fluid communication between the inlet and outlet and the signal pathway transmits a signal of analysis from the analytic region to the outside.

47. A process of claim 46 wherein the device body is fabricated using plastic injection molding.

48. A process of claim 46 wherein the analytic device is fabricated from silicon.

49. A process of claim 46 wherein the analytic device is fabricated from a combination of silicon with plastic or glass.

50. A process of claim 46 wherein the lance is fabricated from metal.

51. A process of claim 46 wherein the lance is fabricated from silicon.

52. A process of claim 46 wherein the lance is fabricated from plastic.

* * * * *